United States Patent
Ruiter

(10) Patent No.: US 7,346,378 B2
(45) Date of Patent: Mar. 18, 2008

(54) LIGHT TRANSMISSION SIMULATOR FOR PULSE OXIMETER

(75) Inventor: Karl A. Ruiter, South Pasadena, CA (US)

(73) Assignee: Pronk Technologies Inc., South Pasadena, CA (US)

(*) Notice: Subject to any disclaimer, the term of this patent is extended or adjusted under 35 U.S.C. 154(b) by 175 days.

(21) Appl. No.: 11/379,763

(22) Filed: Apr. 21, 2006

(65) Prior Publication Data
US 2006/0247507 A1 Nov. 2, 2006

Related U.S. Application Data

(60) Provisional application No. 60/677,251, filed on May 2, 2005, provisional application No. 60/726,639, filed on Oct. 14, 2005.

(51) Int. Cl.
*A61B 5/00* (2006.01)
(52) U.S. Cl. ............ 600/323; 250/252.1; 356/41
(58) Field of Classification Search ............ 600/310, 600/322, 323, 330, 331; 73/1.01; 250/252.1; 356/39, 40, 41
See application file for complete search history.

(56) References Cited

U.S. PATENT DOCUMENTS

| | | | |
|---|---|---|---|
| 5,348,005 A | 9/1994 | Merrick et al. | |
| 5,783,821 A | 7/1998 | Costello, Jr. | |
| 5,784,151 A | 7/1998 | Miller et al. | |
| RE36,620 E | 3/2000 | Costello, Jr. | |
| 6,141,572 A | 10/2000 | Haas | |
| RE37,970 E | 1/2003 | Costello, Jr. | |
| 6,954,664 B2 | 10/2005 | Sweitzer et al. | |

*Primary Examiner*—Eric Winakur
*Assistant Examiner*—Etsub D Berhanu
(74) *Attorney, Agent, or Firm*—Michael Blaine Brooks, P.C.; Michael Blaine Brooks

(57) ABSTRACT

A living tissue light transmission simulator system (208, 308) includes receptors of light (215, 216, 315, 316) in portions of the infrared and red spectral bands and the receptors (215, 216, 315, 316), together with amplification (217, 218, 317, 318), infrared detection (239, 371), spectral separation circuitry (219, 319), and post-separation amplification (220, 221, 338, 339, 340, 320, 321), that may be used to drive at least one light source (222, 223, 322, 361). The living tissue light transmission simulator system (208, 308) includes at least one shutter (225, 235, 324, 363, 450) to mechanically modulate generated light from the at least one driven light source (222, 223, 322, 361) where the modulated light may be directed to a pulse oximeter.

9 Claims, 7 Drawing Sheets

LIGHT TRANSMISSION SIMULATOR FOR PULSE OXIMETER

CROSS-REFERENCE TO RELATED APPLICATION

This application claims the benefit of U.S. Provisional Application Ser. No. 60/677,251, filed May 2, 2005, and U.S. Provisional Application Ser. No. 60/726,639, filed Oct. 14, 2005, the disclosures of which are hereby incorporated herein by reference in their entirety for all purposes.

BACKGROUND

1. Technical Field

The invention, in its several embodiments, pertains to optical devices, systems, and processes for simulating the optical transmission of living tissue, and the present field of endeavor more particularly pertains to light transmission simulators and processes of living tissue for pulse oximeters.

2. State of the Art

Oximeters may be used for measuring the blood saturation oxygen level (SpO2) of living tissue, for example, that of a patient in a diagnostic environment. Typically, the patient inserts a digit into a receiving portion of the oximeter.

Living tissue simulators may include a photodiode and a light emitting source. The simulating unit is configured such that when it is inserted into the sensor of the target oximeter, its photodiode is aligned in opposition with the light emitting diode (LED) of the target oximeter, while its light emitting source is aligned in opposition with the photo detector in the sensor of the target oximeter. The simulating unit may be connected to a simulator main module which can include a comparator circuit, a digital to analog circuit, a light emitter driver circuit, and a processor circuit.

Pulse oximeters detect the oxygenation of arterial blood by using the differential absorption of hemoglobin by red and infa-red light. A pulse oximeter may alternately illuminate living tissue (e.g., one side of a human digit) with alternating flashes of red and infra-red light of constant amplitude and at a repetition rate that is high compared to an expected maximal heartbeat rate. As the heart takes a beat the finger expands and contracts slightly, the optical path length is increased resulting in the attenuation of the light applied to the finger. The attenuated light is captured by a photodetector of the pulse oximter, and thereafter the amplitude modulated light flashes are processed to determine blood oxygen by detecting and processing the red and infa-red heartbeat-modulated signals.

Simulators that may be used to evaluate pulse oximeter performance are often attenuators and amplitude modulators. That is, the pulse oximeter living tissue simulator receives the red and infrared light flashes of the target pulse oximeter and/or their electrical analogues, and attenuates the signals and modulates their amplitudes to generate outputs for the target oximeter similar to the light transmissions of living tissue.

SUMMARY

The present invention, in its several embodiments, includes a living tissue or oxygenated tissue light transmission simulator embodiments having an optical waveguide, where an exemplary simulator embodiment further includes: an infrared receiving element sensitive in at least a portion of the infrared light spectrum and wherein the infrared receiving element may output one or more electrical signals in response to sensed infrared light; a broadband receiving element sensitive in a least a portion of the infrared and red light spectrum wherein the broadband receiving element may output one or more electrical signals in response to sensed broadband light; a separator circuit that separates from the output signal of the broadband receiving element an infrared component signal and a red light component signal and where the separator circuit may output the separated infrared component signal and the separated red light component signal; a first voltage-to-current amplifier, typically responsive to the separator circuit infrared component output signal, where the first voltage-to-current amplifier may output a signal that can drive a first LED; and a first shutter interposed in a light path between the first LED and the optical waveguide, where the first shutter is typically responsive to one or more actuating signals from a processing unit and where the first shutter may mechanically modulate the light emitted from the first LED.

In some embodiments, the first voltage-to-current amplifier of a living tissue light transmission simulator embodiment may be responsive also to the separator circuit red component output signal. In some embodiments, the living tissue simulator embodiment may also include a second voltage-to-current amplifier that may be responsive to the one or more broadband receiving element output electrical signals where the second voltage-to-current amplifier typically has an output signal that can drive a second LED where the driven second LED may transmit at least a portion of its emission into the optical waveguide. In some exemplary embodiments of the living tissue light transmission simulator may also include a second voltage-to-current amplifier that is typically responsive to the separator circuit red component output signal, and the second voltage-to-current amplifier may have an output signal that typically drives a second LED and the living tissue simulator may also include a second shutter interposed in a light path between the second LED and the optical waveguide, where the second shutter is typically responsive to one or more actuating signals from the processing unit and wherein the second shutter may mechanically modulate the light emitted from the second LED. Some exemplary embodiments of the living tissue simulator may further include a third voltage-to-current amplifier that is typically responsive to the one or more broadband receiving element output electrical signals, where the third voltage-to-current amplifier has an output signal that can typically drive a third LED and where the third LED is adapted to transmit at least a portion of its emission into the optical waveguide.

BRIEF DESCRIPTION OF THE DRAWINGS

For a more complete understanding of the present invention and for further features and advantages, reference is now made to the following description taken in conjunction with the accompanying drawings, in which.

DETAILED DESCRIPTION OF THE EXEMPLARY EMBODIMENTS

The present invention in its several embodiments includes is a device for simulating the transmission of light by living tissue that may be used in testing and calibrating of pulse oximeters generally and may be used particularly in the testing and calibrating of pulse oximeters that are used to measure oxygen saturation value (SpO2).

Figure 1:
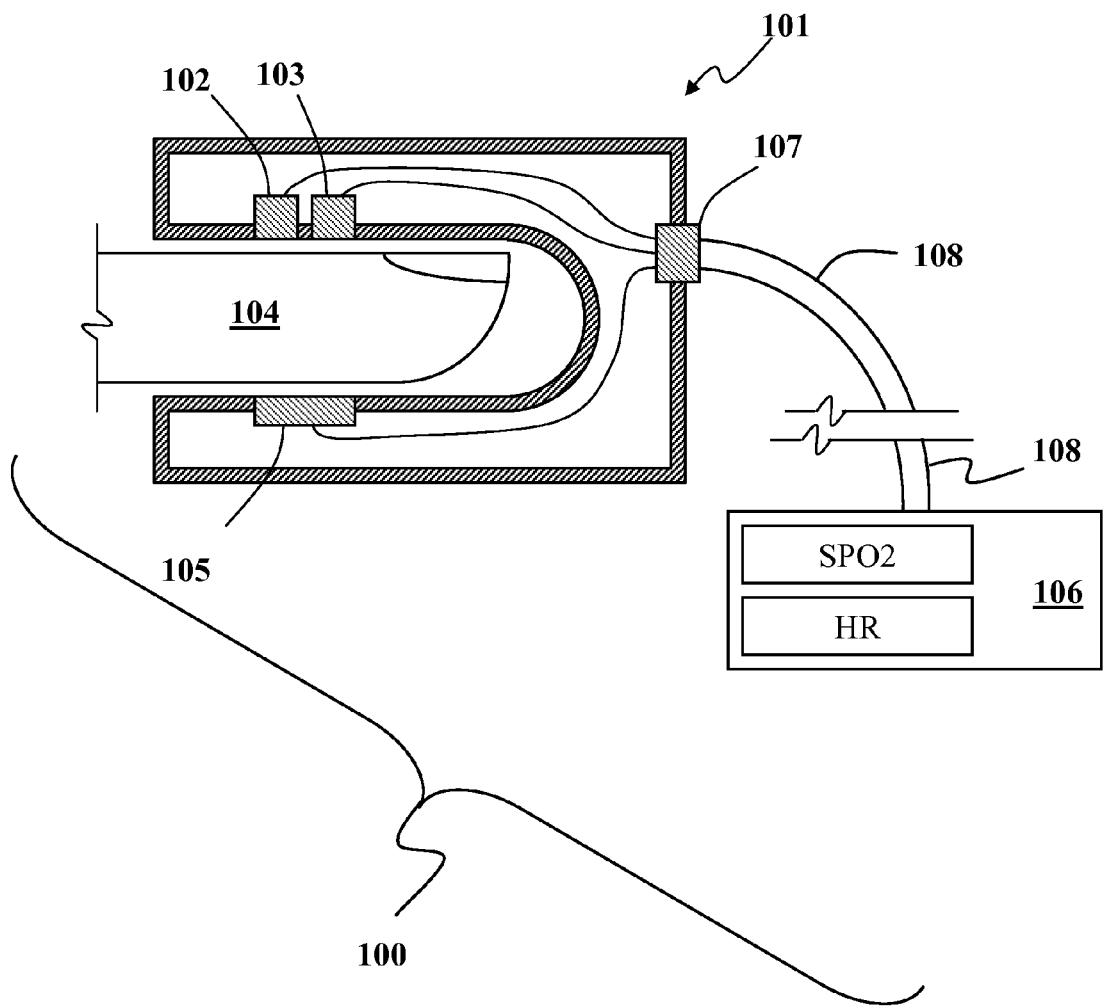
FIG. 1 illustrates a prior art pulse oximeter with a human digit inserted into a portion thereof.

A typical operation of a pulse oximeter is illustrated from the cross-sectional view of the pulse oximeter shown in FIG. 1. The exemplary pulse oximeter under test (100) comprises a patient sensor portion (101) and a processing portion (106) which may be distributed modules or an integrated unit. The patient sensor portion (101) comprises a source of two discrete wavelengths of light—which may include a red light emitting diode (LED) (102) and an infrared (103) LED—as well as a photo-detector (105). During operation with an actual patient, light flashes are emitted from the LEDs (102, 103) pass through some portion of the patients flesh, e.g., a finger (104) or ear lob, and the resultant patient-modulated light signal is received by the photo detector (105). An interface (107) between the patient sensor (101) and the processing portion of the pulse oximeter (106) may be provided as well as a conduit (108) for the signal paths for the LEDs (102, 103) and the photo-detector (105). Logic or process steps internal to the pulse oximeter (106) may then be processed with input such as the detected patient modulated light flashes and the processing portion (106) then calculates the percentage of the patient's hemoglobin which is oxygenated as well as the patient's heart rate via means that are well known to those of ordinary skill in the art. In some pulse oximeters, the two discrete wavelengths of light are passed through the patient's tissue at alternating times, the amount of absorbed light for each wavelength determined, and the ratios of absorbed red and absorbed infrared light AC and DC components are applied to derive the blood oxygen saturation estimate.

Figure 2:
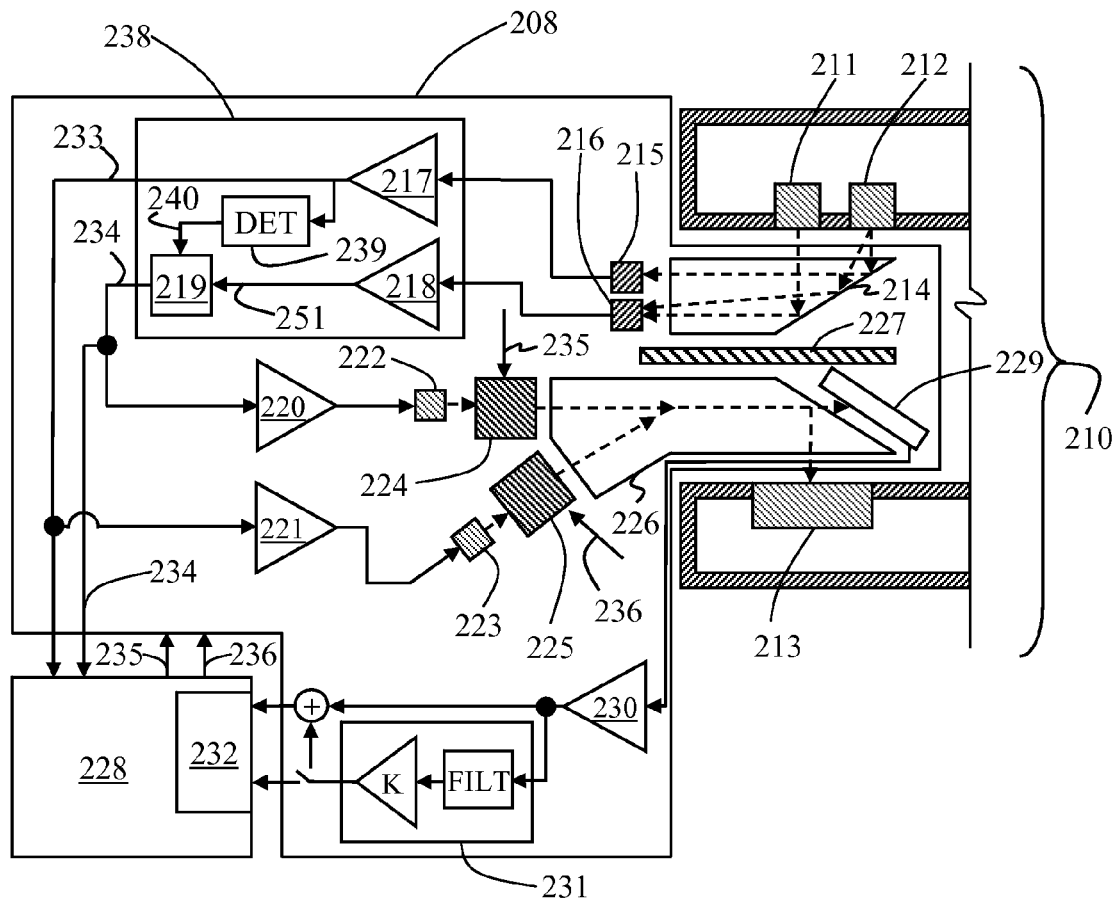
FIG. 2 is a functional schematic diagram of an exemplary living tissue simulator embodiment of the present invention inserted into a portion of a pulse oximeter.

A portion of a simulator of some of the living tissue characteristics of the patient's flesh (104) may be inserted into the patient sensor portion (101) in place of the patient's flesh (104) in order test the pulse oximeter (100). A schematic diagram of an exemplary embodiment of a simulator (208) of the present invention is shown in FIG. 2. The exemplary simulator (208) is adapted to mimic oxygenated tissue for purposes of testing a pulse oximeter. FIG. 2 shows a pulse oximeter patient sensor (210) that includes a red LED (211) and an infrared LED (212) and a photo-detector (213). According to this exemplary embodiment of the present invention, light emitted from the patient sensor's LEDs may be directed by an input light pipe (214), or other optical waveguide or transmission member, to an infrared-only detector, e.g., an infrared-only photodiode (215), and a broadband detector, e.g., a broadband photodiode (216). The signals from the photo diodes may be amplified by amplifier bank (238)—including in this example a first amplifier (217) and a second amplifier (218)—and the amplified infrared-only signal (233) may be thereafter detected by or otherwise identified with a threshold detection circuit (239). The detected infrared-only signal (240) may then used to strip the infrared component from the amplified broadband signal (251) via a stripping circuit or processor (219) to produce or otherwise isolate a red-only signal (234). Exemplary detection circuitry, i.e., determining whether the reference infrared signal is above a baseline threshold, and exemplary stripping circuitry, i.e., extracting the red-only signal from an otherwise combined red and infrared signal during the state of reference infrared signal detection, are disclosed below.

The red-only signal (234) and infrared-only signal (233) are then used to drive voltage to current amplifiers—including a third amplifier, e.g., a first voltage-to-current amplifier (220), for the red-only signal (234) and a fourth amplifier, e.g., a first voltage-to-current amplifier (221), for the infrared-only signal (233) which may in turn respectively drive at least two output LEDs—including a first simulator LED (222) for the output of the third amplifier (220) and a second simulator LED (223) for the output of the fourth amplifier (221)—which reproduce the intensities of the detected red and infrared light flashes but with greater spatial separation, i.e., a spatial separation sufficient to separately modulate the red and infrared light flashes which either or both may function as carrier light signal. The light signals from the output LEDs (222, 223) may be each be passed through a respective mechanical modulating unit, in this example, they include two mechanical shutters—including a first shutter (224) proximate to the first simulator LED (222) and a second shutter (225) proximate to the second simulator LED (223), respectively—which may be triggered or controlled by steps and tests processed by or executed by a processing unit, such as a microprocessor (228), via shutter control signals (235, 236) and thereby generate pulsed versions of the detected red flashes and infrared flashes by partially and/or periodically blocking the radiation from the output of the first simulator LED (222) and the second simulator LED (223). By controlling the rate and relative size of the shutter pulses, the microprocessor (228) may be adapted to effect the simulation of a wide variety of patient saturation values and pulse rates. Pulsed light from the output of the shutters (224, 225) is illustrated as being combined via an output light pipe (226) and then directed to a photo-detector (213) illustrated on a portion the pulse oximeter's patient sensor (210). Light emanating from the first LED (211) and the second LED (212) of pulse oximeter's patient sensor (210) may be prevented from reaching the sensor's photo detector (213) by an opaque barrier (227).

During initial power-up, the microprocessor (228) may perform a calibration of the optical shutters (235, 236) via an LED override mechanisms using an infrared-only signal (234) and the red-only signal (234), a feedback photo-detector (229) connected or proximate to the output light pipe (226), an amplifier (230) and an analog-to-digital (A2D) converter (232) to sequentially force into an on state the red and infrared output LEDs (222, 223) while driving the shutters (235, 236). Additional amplification and filter circuitry (231), that may include bandpass filtering, may be employed to allow for refining the measurements of shutter pulse sizes that may be used to adjust the durations of the processor (228) shutter commands (235, 236).

Figure 3A:
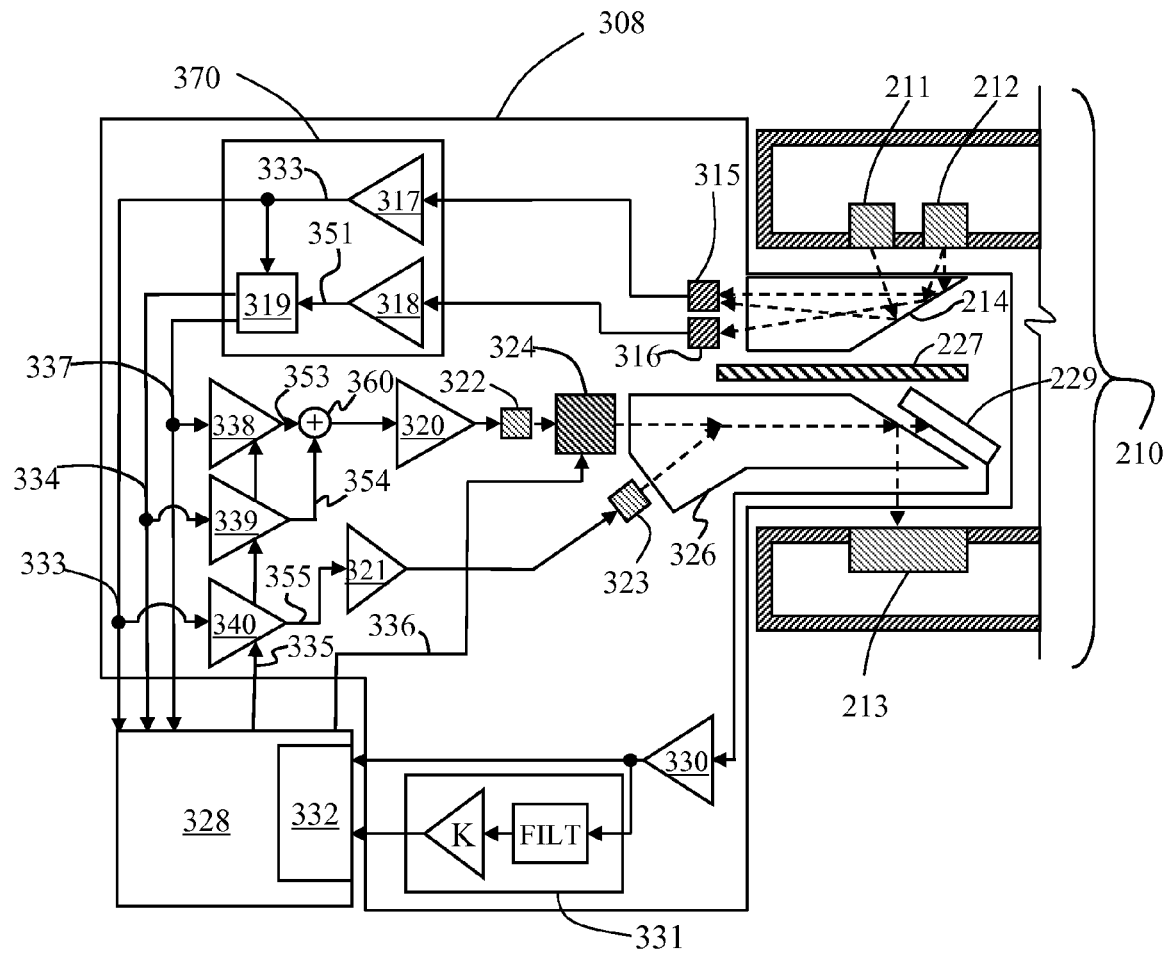
FIG. 3A is a function schematic diagram of another exemplary living tissue simulator embodiment of the present invention inserted into a portion of a pulse oximeter.

A schematic diagram of a second exemplary simulator embodiment (308) of the present invention is shown in FIG. 3A. The exemplary simulator (308) of this exemplary embodiment is illustrated as being adapted to mimic oxygenated tissue for purposes of testing a pulse oximeter. As in FIG. 2, FIG. 3A again shows a portion of a pulse oximeter patient sensor (210), comprising a red LED (211) and an infrared LED (212) and a photo-detector (213). According to this second exemplary embodiment of the present invention, light emitted from the patient sensor's LEDs (211, 212) may be directed by an input light pipe (214) to an infrared-only reference photodiode (316) and a broadband photodiode (315). The signals from the infrared-only photodiode (316) and the broadband photodiode (315) are amplified by amplifier bank (370)—including a first amplifier (317) for the signals from the broadband photodiode (315) and a second amplifier (318) for the signals from the infrared-only broadband diode (316)—and the amplified infrared-only reference signal (351) may used in conjunction with the amplified broadband signal (333) by the detection and separator circuitry (319) to produce or otherwise isolate a red-only signal (337) and an infrared-only signal (334).

The red-only signal (337) and infrared-only signal (334) may then be sent through selectable gain stages, e.g., a first selectable gain stage (338) for the red-only signal and a second selectable gain stage (339) for the infrared-only signal, where the further amplified red-only signal (353) and the further amplified infrared-only signal (354) are summed (360), and the summed signal sent to drive a voltage-to-current amplifier (320), which in turn may output a signal that drives a first output LED (322), producing light flashes called the AC optical signal. This AC optical signal is then mechanically modulated with a physiological signal via a shutter mechanism (324) that may be controlled by steps and/or tests executed by a microprocessor (328) via shutter control signals (336) and the modulated AC optical signal may then be sent to the output light pipe (326). Accordingly, the mechanical shutter mechanism (324) outputs modulated versions of the AC optical signal by partially blocking and/or periodically blocking the radiation from the output LED (322).

Additionally, the amplified broadband signal (333) may be sent through a third selectable gain stage (340), and then the further amplified broadband signal (355) may be sent to a voltage-to-current amplifier (321), which in turn outputs a signal that drives a second output LED (323), producing light flashes called the DC optical signal. The modulated AC optical signal and the DC optical signals may then be combined in the output light pipe (326) and directed to the sensor's photo-detector (213). Also, light directly from the patient sensor's LEDs (211) and (212) may be prevented from reaching the sensor's photo-detector (213) by an opaque barrier (227).

Figure 3B:
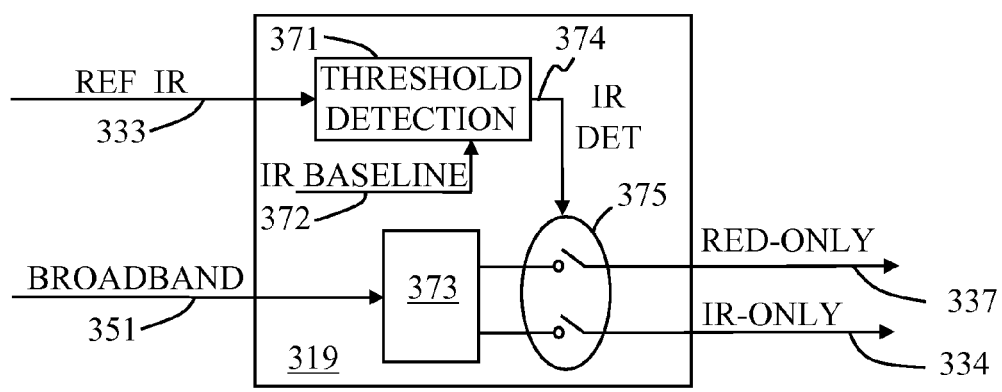
FIG. 3B is a functional schematic diagram of an exemplary detection and separator circuit.

FIG. 3B illustrates an example of a functional schematic of the detection and separator circuitry (319) where the amplified reference infrared signal (351) and the amplified broadband signal (3533) are taken into the exemplary detection and separator circuit (319). The amplified broadband signal (333) may be separated into constituent components that may include a red-only signal (337), which may be used in the exemplary embodiment of FIG. 2 above, and an infrared-only signal (334). A threshold detection circuit (371) may take in an infrared baseline value or have a preset infrared baseline value (372) that may be compared with the incoming reference infrared signal (351) and thereby generate an infrared detection signal (374) when the amplified reference infrared signal (351) is above the threshold value established by the infrared baseline value (372). A portion of the detection and separator circuitry (319) may be responsive to the infrared detection signal (374) and select in alternative fashion, i.e., based on the state of the infrared detection signal (374), either the red-only signal (337) or the infrared-only signal to be output from the exemplary detection and separator circuit (319).

Figure 3C:
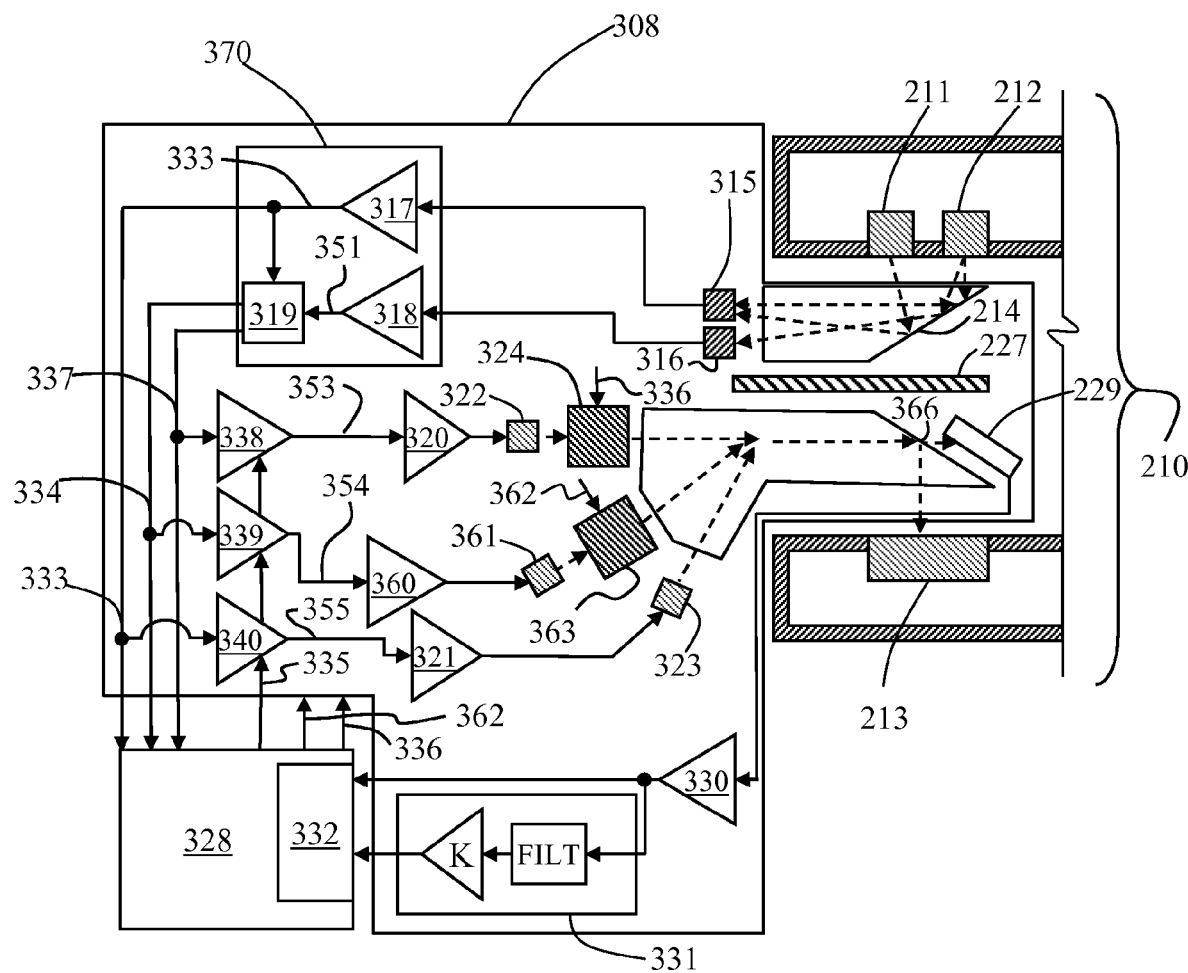
FIG. 3C is a functional schematic diagram of another exemplary living tissue simulator embodiment of the present invention inserted into a portion of a pulse oximeter.

FIG. 3C illustrates a third exemplary embodiment where the red-only signal (337) and infrared-only signal (334) are each sent through a respective selectable gain stages, e.g., a first selectable gain stage (338) for the red-only signal and a second selectable gain stage (339) for the infrared-only signal, where the further amplified red-only signal (353) is sent to drive a first voltage-to-current amplifier (320) which in turn outputs a signal that drives a first output LED (322) that may then in turn produce light flashes called the AC red-only signal. As in the exemplary embodiment described in FIG. 3A, the AC red-only signal is then mechanically modulated with a physiological signal via a first shutter mechanism (324) proximate to the first output LED (322). The first shutter mechanism (324) may be controlled by steps and/or tests executed by a processing unit, such as microprocessor (328), via shutter control signals (336) and the modulated AC red-only signal may then be sent to the output light pipe (366). Accordingly, the first mechanical shutter mechanism (324) creates modulated versions of the AC red-only signal by partially blocking and/or periodically blocking the radiation from the first output LED (322). The further amplified infrared-only signal (354) is used to drive a second voltage-to current amplifier (360), which in turn outputs a signal that drives a second output LED (361), producing light flashes called the AC infrared-only signal. As with the AC red-only signal, this AC infrared-only signal is then mechanically modulated with a physiological signal via a second shutter mechanism (363) that may be controlled by steps and/or tests executed by the exemplary microprocessor (328) via shutter control signals (362) and the modulated AC infrared-only signal may then be sent to the output light pipe (366). Accordingly, the second mechanical shutter mechanism (363) produces modulated versions of the AC infrared-only signal by partially blocking the radiation from the output LED (361). As described in the exemplary embodiment of FIG. 3A, the exemplary embodiment of FIG. 3C has an amplified broadband signal (333) that may be sent through a third selectable gain stage (340), and as a further amplified broadband signal (355) to a third voltage-to-current amplifier (321), which in turn outputs a signal that drives a second output LED (323). The second output LED (323), responsive to the driving signals from the third voltage-to-current amplifier (321), may produce light flashes called the DC optical signal. The modulated AC red-only signal, modulated AC infrared-only signal and the DC optical signal may then combined in the output light pipe (366) and directed to the sensor's photo-detector (213).

For any of the exemplary embodiments including those illustrated in FIGS. 2, 3A and 3B, during initial power-up, the microprocessor (228, 328) may be adapted to perform a calibration of the optical shutters and output LEDs via override mechanisms which allow it to override the further amplified red-only signal (353), the amplified infrared-only signal (354), and a further amplified broadband signal (355). The calibration process also may taken in signals from a feedback photo-detector (229) connected to the output light pipe, an amplifier (230, 330) and an analog-to-digital (A2D)

converter (232, 332) to detect and measure the optical signals generated. Additional amplification and filtration circuitry (231, 331) may be employed to allow for more precise measurement of shutter pulse sizes.

Figure 4:
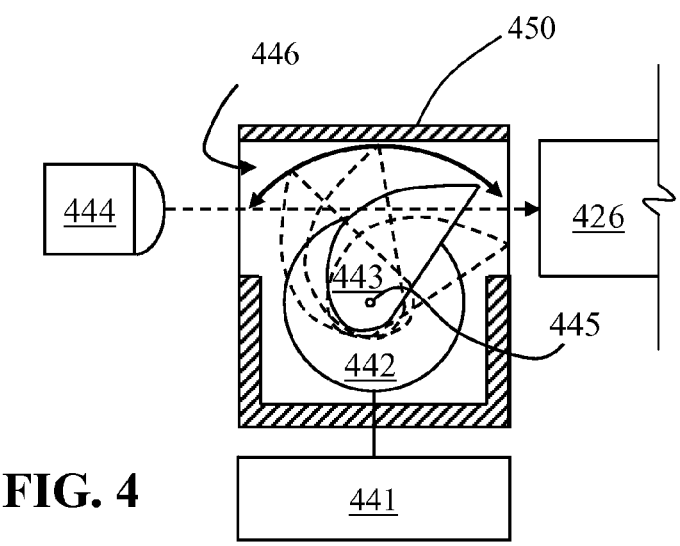
FIG. 4 is a cross-sectional view of an exemplary optical shutter of the present invention.

FIG. 4 shows an exemplary embodiment of an optical shutter 450 of the present invention. In this example, the microprocessor (441) controls a stepper motor (442) which drives a cam (443) to rotate and thereby change the size of an aperture (446) which causes differing amounts of the output radiation of the output LED (444) to be blocked or passed, depending on the rotary position of the motor shaft (445). In some embodiments, the cam (443) is a linear cam that varies the size of a light-transmitting aperture (446) linearly with respect to the angular position of the cam (443). In some embodiments, the shutter mechanism may comprise a motor which drives a cam which causes the rotation of a pivoting arm, the far end of which partially blocks the output light of the LED. In some embodiments, the shutter mechanism may comprise a motor which drives a first pulley, which in turn drives a belt, which in turn drives a second pulley, to which may be attached a flag or slotted disk which may block or partially block or otherwise obstruct, occlude or filter the output light of the LED.

Figure 5A:
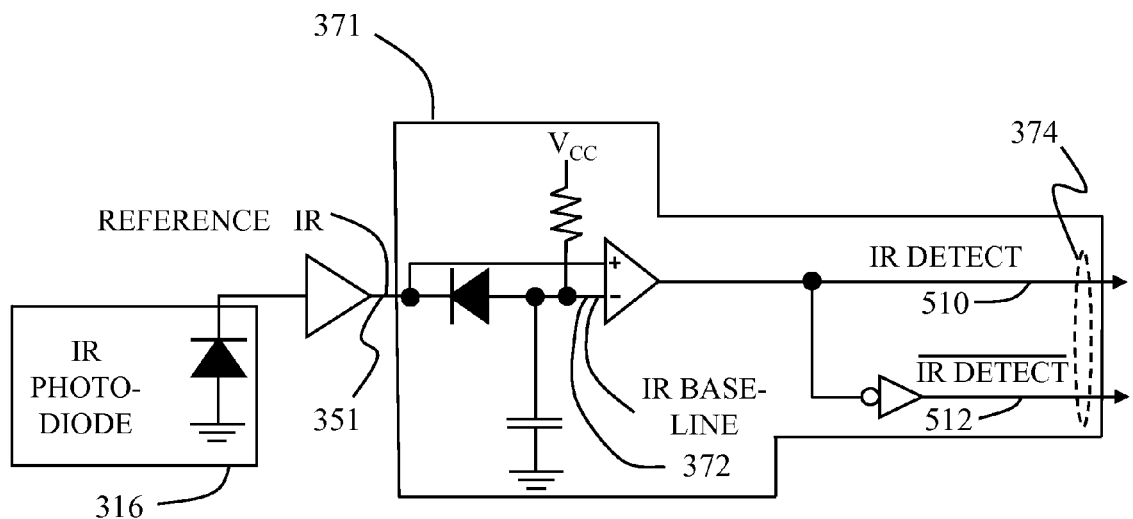
FIG. 5A is a functional schematic diagram of an exemplary infrared detector circuit of the present invention.
Figure 5B:
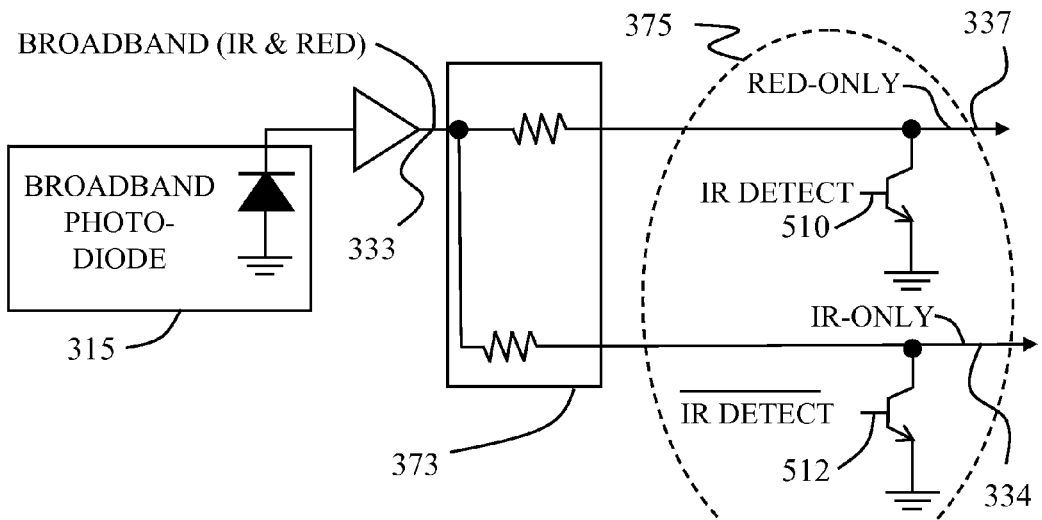
FIG. 5B is a functional schematic diagram of an exemplary separator circuit of the present invention.

FIG. 5A shows an exemplary embodiment of the detection portion of a detection and separator circuit (319) for separating the amplified broadband signal (333) into a red-only signal (337) and an infrared-only, or IR-only, signal (334). In this example, an amplified infrared reference signal (351) may be compared with a threshold value representing an infrared baseline value (372) and when the threshold is achieved, an infrared detection signal 510 is output and otherwise an infrared not detected signal 512 is output. The amplified broadband signal (333) includes both an infrared and a red signal in combination that may be sensed or acquired by the broadband photodiode (315). FIG. 5B shows that the amplified broadband signal (333) may be separated by separating circuitry (373) and circuitry (375) responsive to the detected reference infrared state (374) may then output either the red-only signal 375 or the infrared-only signal (334). Accordingly in this exemplary embodiment of FIG. 5B, the separator circuit functions by comparing the reference IR signal to an IR Baseline signal to generate an IR detect signal which then allows the current signal amplified broadband signal to pass out to one of either the red-only signal (337) or IR-only signal (334).

Figure 6:
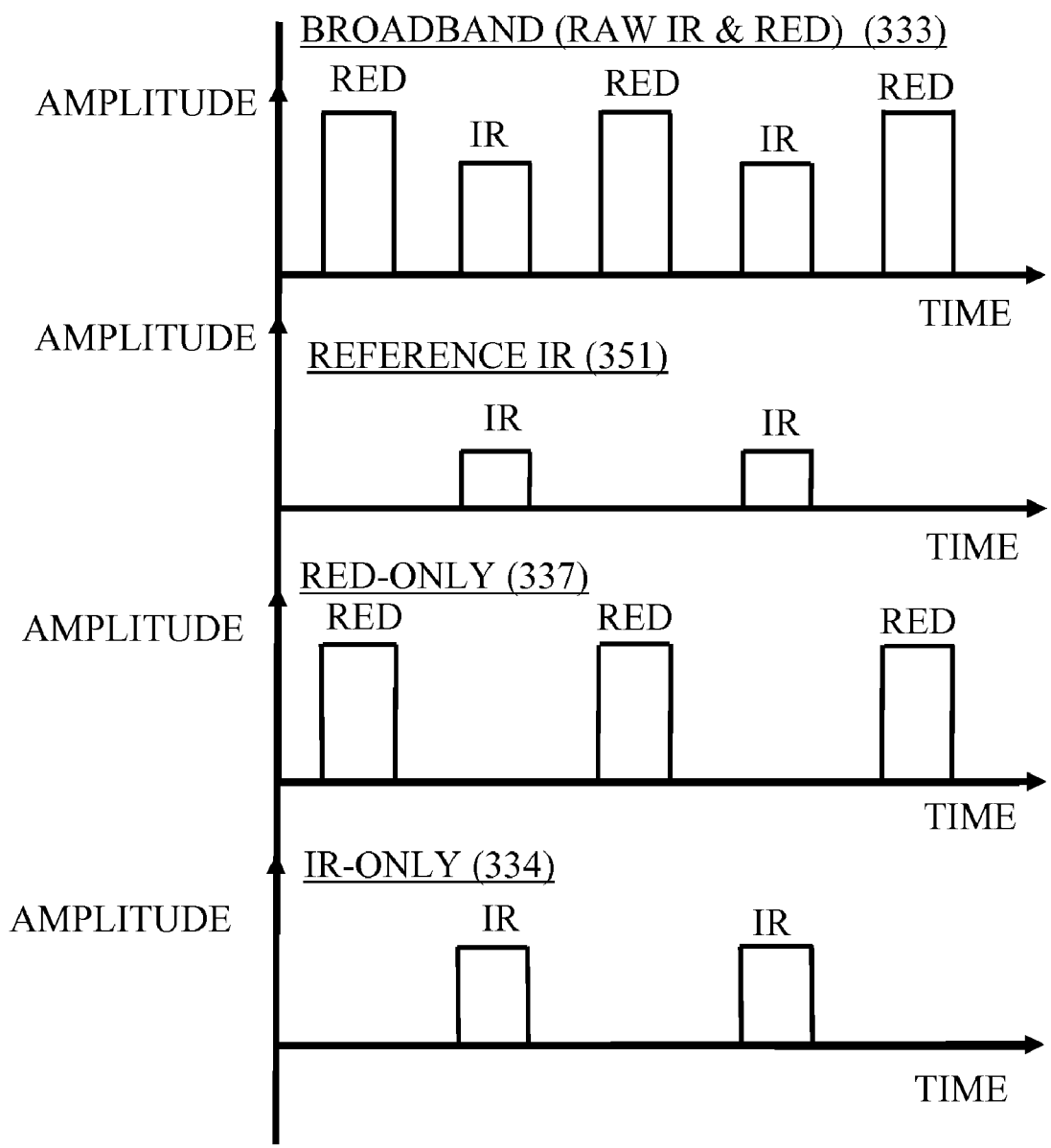
FIG. 6 is an exemplary signal timeline of the present invention.

FIG. 6 illustrates an exemplary timeline of signal of interest. The amplified broadband signal (333) is shown as including infrared (IR) pulses interposed in time between red pulses. The amplified reference infrared signal (351) is shown as including only infrared signals temporally correlated with the IR components of the amplified broadband signal (333). The red-only signal (337) is shown as the amplified broadband signal (333) after the IR pulses have been removed. The infrared-only signal (334) is shown as the amplified broadband signal (333) after the red-only pulses have been removed.

Figure 7:
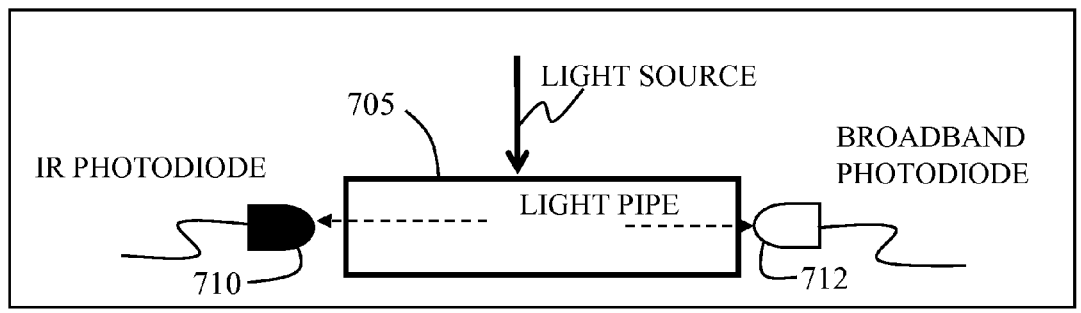
FIG. 7 is another embodiment of photodiode placement geometry of the present invention.
Figure 8:
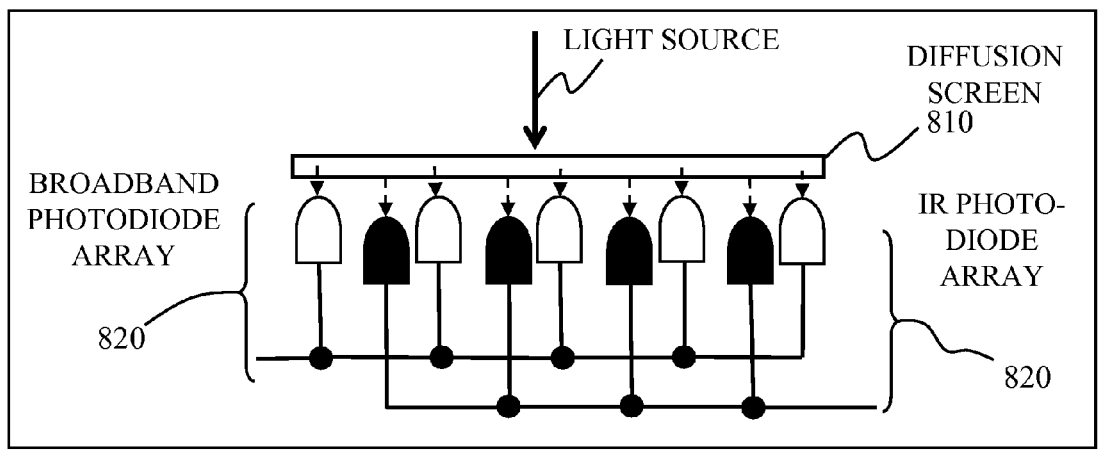
FIG. 8 is another embodiment of the photodiode quantity and arrangement geometry of the present invention.
Figure 9:
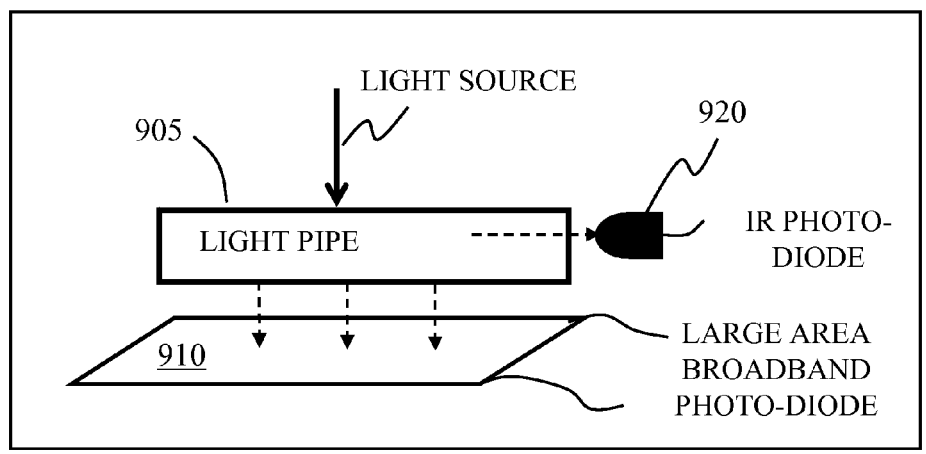
FIG. 9 is another embodiment of the photodiode type and arrangement geometry of the present invention.

FIGS. 7-9 show additional embodiments of the light collection system of the oxygenated tissue simulators (208, 308) of FIGS. 2, 3A and 3C. In FIG. 7, the simulator (208, 308), as disclosed by example in FIGS. 2, 3A and 3C, collects light from the red LED (211) and an infrared LED (212) using an elongated light pipe (705) with the infrared photodiode (710) and broadband photodiode (712) on either end of the elongated light pipe (705). In FIG. 8, the light from the pulse oximeter (210), as disclosed by example in FIGS. 2, 3A and 3C, impinges on a diffusion screen (810) and the diffused light collected by a one or two dimensional array of photodiodes including one or more infrared photodiodes and one or more broadband photodiodes. In FIG. 8, a broadband photodiode array (820) and an infrared photodiode array (830) are interposed between the light source and a diffusion screen (810). In FIG. 9, the light from the pulse oximeter (210), as disclosed by example in FIGS. 2, 3A and 3B, is collected by the light pipe (905) and distributed to a large area broadband photodiode (910) that may be placed proximate and coextensive with the light pipe (905) and the light may also be transmitted via the light pipe (905) to an infrared photodiode (920).

Although the description above contains many specifications, these should not be construed as limiting the scope of the invention but as merely providing illustrations of some of the presently preferred embodiments of this invention.

What is claimed is:

1. An oxygenated tissue simulator adapted to test a pulse oximeter with one or more interrogating light signals, the interrogating light signals comprising a red light signal and an infrared light signal, the tissue simulator comprising:
   one or more detectors adapted to convert the red light signal and infrared light signal of the pulse oximeter into at least one electrical signal;
   one or more light sources adapted to convert the at least one electrical signal into at least one carrier light signal;
   means for modulating the at least one carrier light signal to simulate oxygenated tissue; and
   means for transmitting the at least one modulated carrier light signal to the pulse oximeter.

2. The oxygenated tissue simulator of claim 1, wherein the oxygenated tissue simulator further comprises one or more amplifiers adapted to amplify the at least one electrical signal.

3. The oxygenated tissue simulator of claim 1, wherein means to modulate the at least one carrier light signal comprises one or more shutters.

4. The oxygenated tissue simulator of claim 3, wherein each of the one or more shutters comprises a stepper motor.

5. A living tissue light transmission simulator comprising an optical waveguide, the simulator further comprising:
   an infrared receiving element sensitive in at least a portion of the infrared light spectrum wherein the infrared receiving element is adapted to output one or more electrical signals in response to sensed infrared light;
   a broadband receiving element sensitive in a least a portion of the infrared and red light spectrum wherein the broadband receiving element is adapted to output one or more electrical signals in response to sensed broadband light;
   a separator circuit adapted to separate from the output signal of the broadband receiving element an infrared component signal and a red light component signal wherein the separator circuit is adapted to output the separated infrared component signal and the separated red light component signal;
   a first voltage-to-current amplifier, responsive to the separator circuit infrared component output signal, having an output signal adapted to drive a first light emitting diode (LED); and
   a first shutter interposed in a light path between the first LED and the optical waveguide, wherein the first shutter is responsive to one or more actuating signals from a processing unit and wherein the first shutter is adapted to mechanically modulate the light emitted from the first LED.

6. The living tissue light transmission simulator of claim 5 wherein the first voltage-to-current amplifier is further responsive to the separator circuit red component output signal.

7. The living tissue light transmission simulator of claim 6 further comprising a second voltage-to-current amplifier, responsive to the one or more broadband receiving element output electrical signals, the second voltage-to-current amplifier having an output signal adapted to drive a second LED wherein the second LED is adapted to transmit at least a portion of its emission into the optical waveguide.

8. The living tissue light transmission simulator of claim 5 further comprising:
   a second voltage-to-current amplifier, responsive to the separator circuit red component output signal, having an output signal adapted to drive a second LED; and
   a second shutter interposed in a light path between the second LED and the optical waveguide, wherein the second shutter is responsive to one or more actuating signals from the processing unit and wherein the second shutter is adapted to mechanically modulate the light emitted from the second LED.

9. The living tissue light transmission simulator of claim 8 further comprising a third voltage-to-current amplifier, responsive to the one or more broadband receiving element output electrical signals, the third voltage-to-current amplifier having an output signal adapted to drive a third LED wherein the third LED is adapted to transmit at least a portion of its emission into the optical waveguide.

* * * * *